US00PP31469P3

(12) United States Plant Patent
Conev et al.

(10) Patent No.: US PP31,469 P3
(45) Date of Patent: Feb. 25, 2020

(54) SHRUB ROSE PLANT NAMED 'VLR001'

(50) Latin Name: *Rosa hybrida*
Varietal Denomination: VLR001

(71) Applicants: Vineland Research and Innovation Centre, Vineland Station (CA); Canadian Nursery Landscape Association, Milton, Ontario (CA)

(72) Inventors: Rumen Conev, Vineland Station (CA); Parminderjit Sandhu, Vineland Station (CA)

(73) Assignees: VINELAND RESEARCH AND INNOVATION CENTRE, Vineland Station (CA); Canadian Nursery landscape Association, Milton, Ontario ( * ) Notice: Subject to any disclaimer, the term of this patent is extended or adjusted under 35 U.S.C. 154(b) by 30 days.

(21) Appl. No.: 15/932,090

(22) Filed: Feb. 2, 2018

(65) Prior Publication Data

US 2019/0182999 P1 Jun. 13, 2019

(30) Foreign Application Priority Data

Mar. 6, 2017 (CA) ..... PBR 17-9114

(51) Int. Cl.
*A01H 5/02* (2018.01)
*A01H 6/74* (2018.01)

(52) U.S. Cl.
USPC ..... Plt./105
CPC ..... *A01H 6/749* (2018.05)

(58) Field of Classification Search
USPC ..... Plt./105
See application file for complete search history.

*Primary Examiner* — Anne Marie Grunberg
(74) *Attorney, Agent, or Firm* — Buchanan Ingersoll & Rooney PC

(57) ABSTRACT

A new and distinct variety of shrub rose plant herein referred to by its cultivar name, 'VLR001', is provided that abundantly forms on a continuous basis attractive single to semidouble formed, orange-red colored blossoms. The plant exhibits an upright and compact bush growth habit. The vegetation is vigorous. Tolerance to black spot, downy mildew, and rust is displayed. The plant is well suited for providing attractive ornamentation in the landscape.

5 Drawing Sheets

Figure 1:
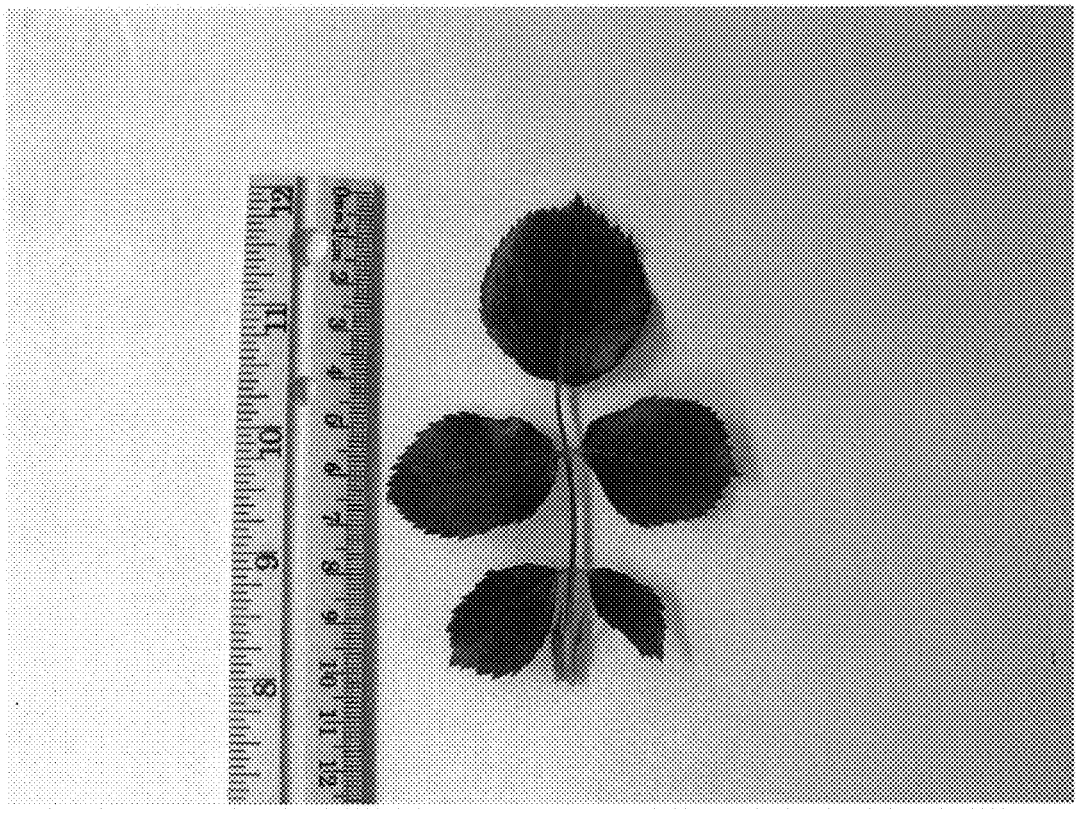

Botanical/commercial classification:
Latin name—*Rosa hybrida.*
Common name—Shrub Rose Plant.
Varietal denomination—'VLR001'.

CROSS-REFERENCE TO RELATED APPLICATIONS

This application claims priority Plant Breeders' Rights Application Number 17-9114, which was filed in Canada on Mar. 6, 2017, of which the content of is hereby expressly incorporated by reference in its entirety for all purposes.

SUMMARY OF THE INVENTION

The new and distinct variety of *Rosa hybrida* shrub rose plant was created by artificial pollination wherein two parents which previously had been studied were crossed in the hope that they would contribute the desired characteristics. The female parent (i.e., the seed parent) of the new variety was the '20ALFR05' variety (non-patented in the United States). The male parent (i.e., the pollen parent) was the '27YSP0412' variety (non-patented in the United States).

The parentage of the new variety can be summarized as follows:

'20ALFR05'×'27YSP0412'.

The seeds resulting from the above pollination were sown and small plants were obtained which were physically and biologically different from one another. Seedlings were evaluated and a single seedling possessing desired characteristics was identified.

It was found that the new shrub rose plant of the present invention possesses the following combination of characteristics:

(a) abundantly and continuously forms attractive single to semidouble formed orange-red blossoms,
(b) exhibits an upright and compact bush growth habit,
(c) forms attractive green foliage with a smooth texture, and
(d) is well suited for growing as attractive ornamentation in the landscape.

The new variety well meets the needs of the horticultural industry and can be grown to advantage in the landscape, including parks, gardens, public areas, and residential landscapes, where attractive ornamentation is to be provided.

The new variety can be readily distinguished from its ancestors. More specifically, while the new variety displays orange-red colored flowers, the '20ALFR05' variety (i.e., the seed parent) display dissimilar pink colored flowers and the '27YSP0412' variety (i.e., the pollen parent) displays dissimilar yellow colored flowers. Moreover, the new variety can be readily distinguished from non-parental related similar varieties. For example, the 'Morden Sunrise' variety (U.S. Plant Pat. No. 13,969) is shorter, exhibits a higher number of petals, and produces a darker green colored leaf compared to the new variety; and the new variety displays orange-red colored blossoms, whereas the 'Morden Sunrise' variety displays yellow-orange colored blossoms.

The characteristics of the new variety have been found to be homogeneous and stable and to be strictly transmissible from one generation to another by asexual propagation through the rooting of cuttings at Vineland Station, Ontario, Canada. Accordingly, the new variety reproduces in a true-to-type manner by such asexual propagation.

The new variety has been named 'VLR001', and is being marketed under the Chinook Sunrise Trademark.

BRIEF DESCRIPTION OF THE PHOTOGRAPH

The accompanying photographs show as nearly true as it is reasonably possible to make the same, in a color illustration of this character, typical specimens of the plant parts of the new variety. The illustrated rose plants of the new variety were approximately 3.5 years of age and were observed during August thru October of 2017 while growing outdoors in the ground on their own roots at Vineland Station, Ontario, Canada.

FIG. 1—illustrates a specimen of a leaf—plan view—upper surface; dimensions in centimeters are indicated at the left of the photograph.

Figure 2:
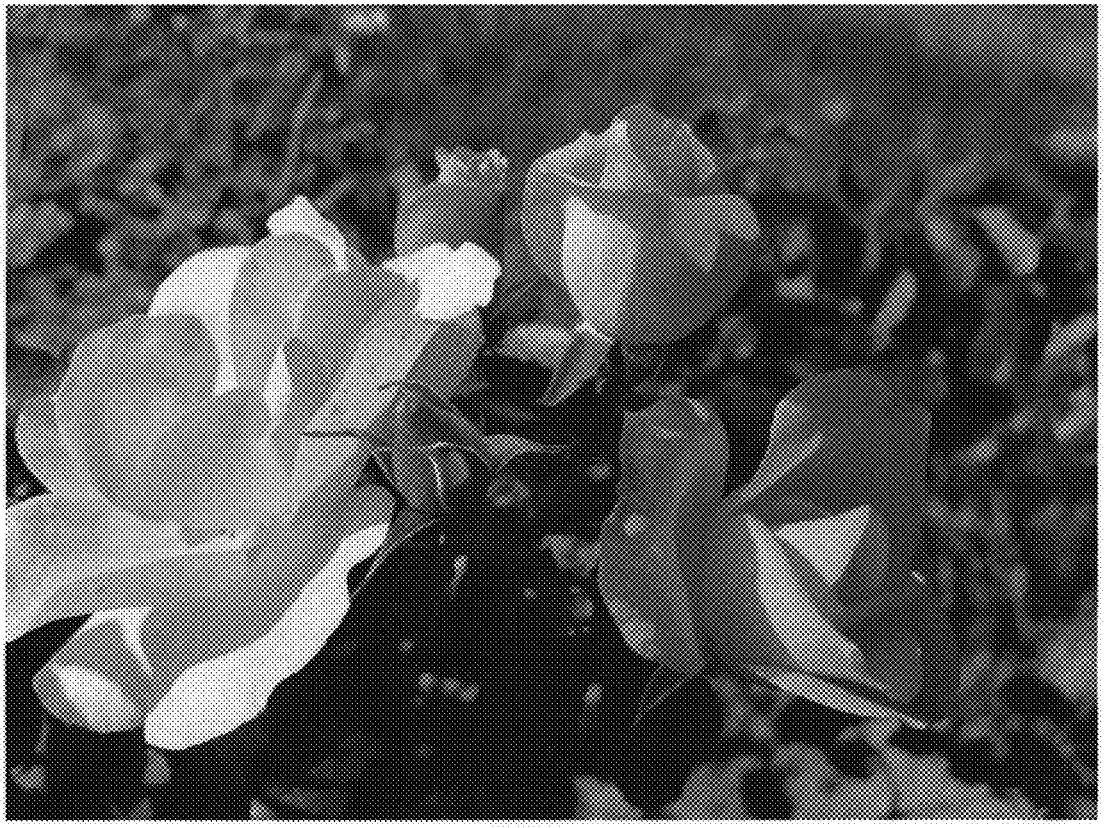

FIG. 2—illustrates a close enlarged view of the attractive orange blossoms with a newly-opened blossom being shown at the top and a mature fully-opened blossom at the bottom left on a plant growing outdoors.

Figure 3:
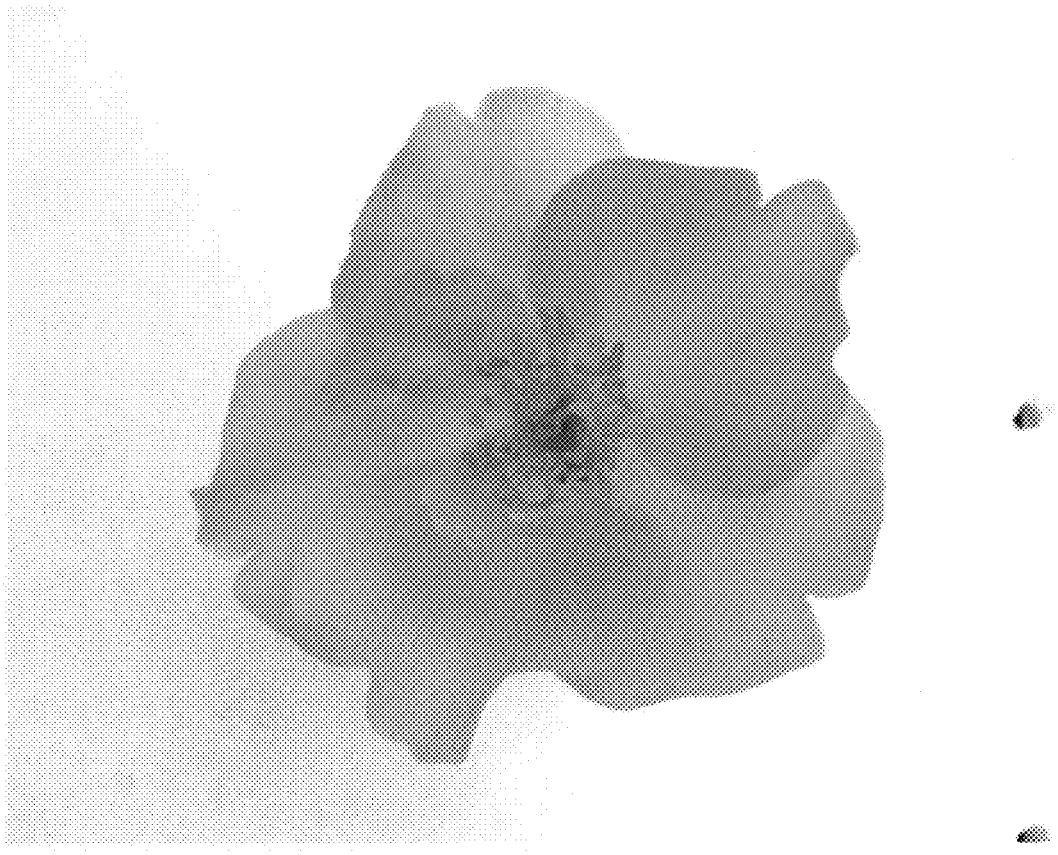

FIG. 3—illustrates a specimen of a fully open flower—plan view—obverse.

Figure 4:
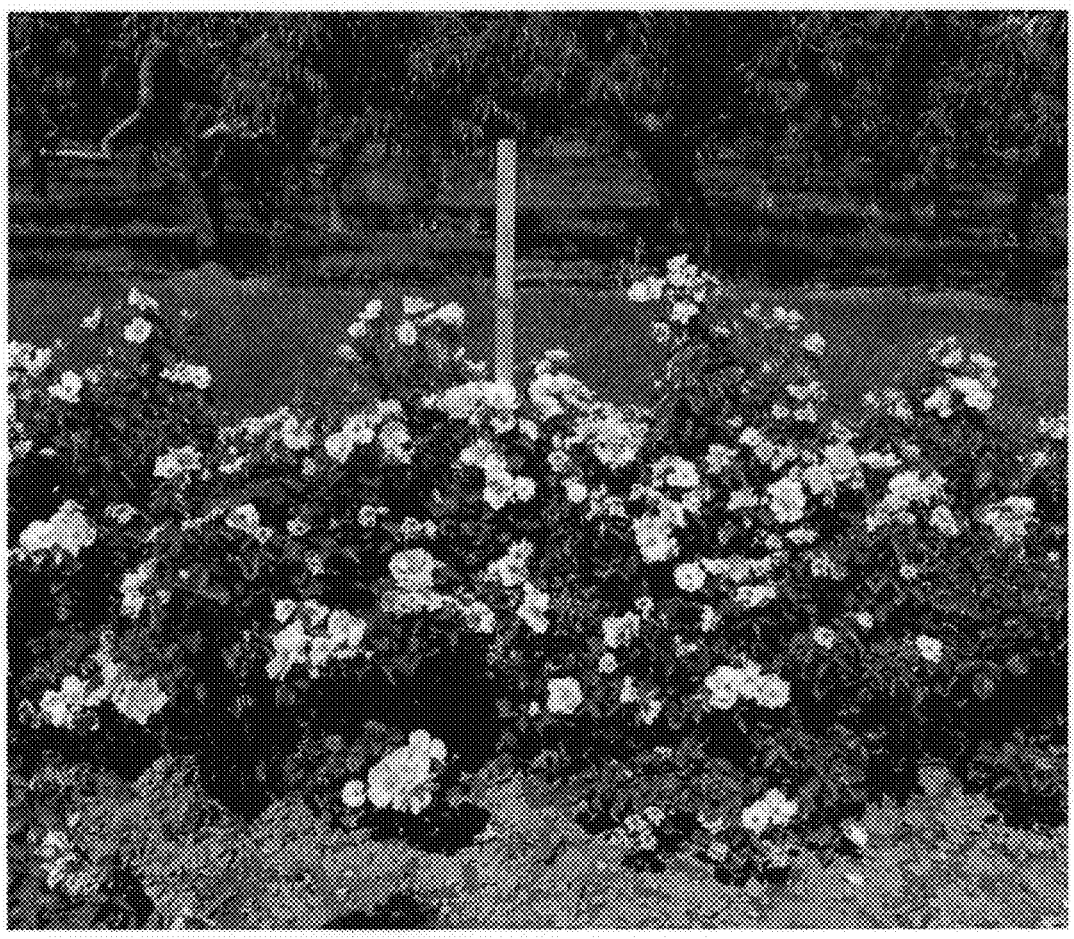

FIG. 4—illustrates an abundantly flowering rose plant growing outside.

Figure 5:
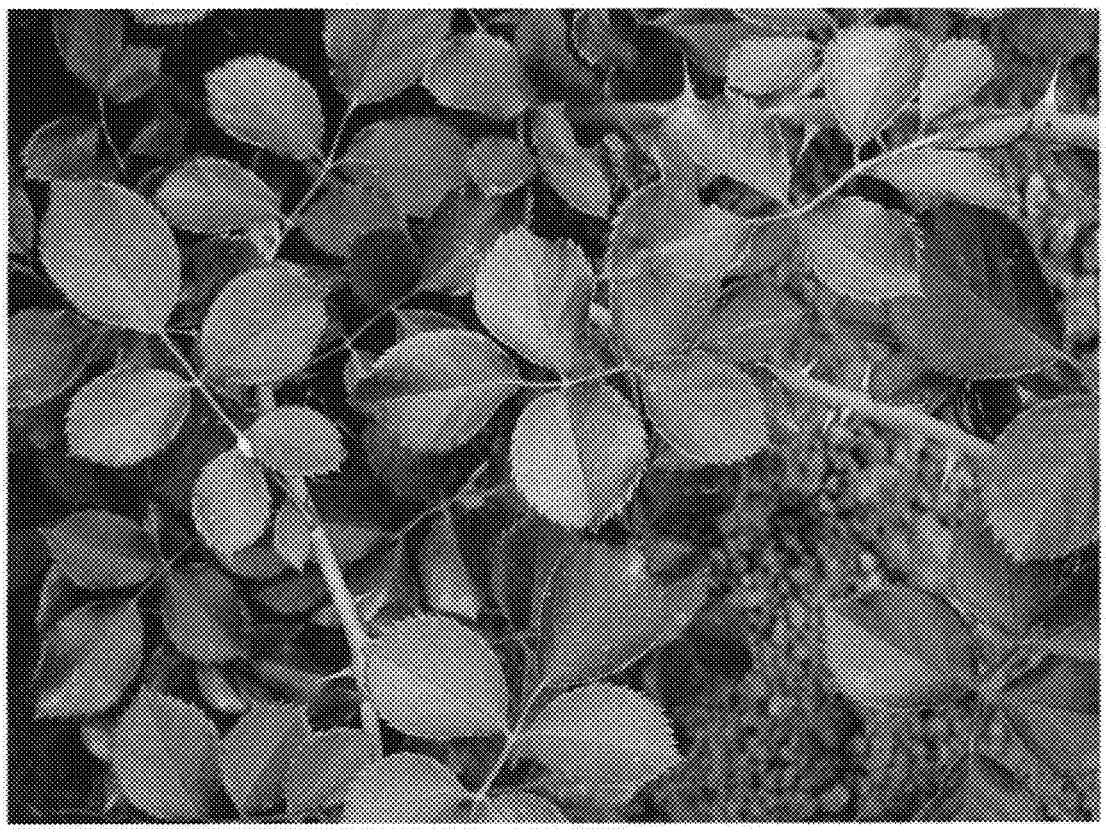

FIG. 5—illustrates a specimen of a plant growing outside; top view of the foliage and branches.

DETAILED BOTANICAL DESCRIPTION

The chart used in the identification of the colors is that of The Royal Horticultural Society ("R.H.S.") (R.H.S. Colour Chart, Fifth Edition). The description is based on the observation of plants 3.5 years of age, which were pruned in the Spring of 2017, during August thru October of 2017 while growing outdoors in the ground on their own roots at Vineland Station, Ontario, Canada.

Class: Shrub Rose.

Plant:

*Growth habit*.—Upright and compact bush.

*Height*.—Approximately 154 cm on average.

*Width*.—Approximately 146 cm on average.

Branches:

*Color*.—Commonly near Yellow-Green Group 144A on young stems and commonly near Yellow-Green Group 146B on mature stems/old wood.

*Stems*.—Main stems: diameter is approximately 9.8 mm on average. Secondary stems: diameter is approximately 4.9 mm on average.

*Thorns*.—Young thorn: length is approximately 6.0 mm on average; width at base is approximately 2.4 mm on average; and color is commonly near Yellow-Green Group N144A. Mature thorn: length is approximately 8.6 mm on average; width at base is approximately 4.9 mm; and color is commonly near Red-Purple Group 59A.

Foliage:

*Number of leaflets*.—Commonly 5-7.

*Terminal leaflet size*.—Approximately 4.2 cm on average in length and approximately 2.5 cm on average in width.

*Lower leaflet size*.—Approximately 2.5 cm on average in length and approximately 1.88 cm on average in width.

*Overall leaf size*.—Approximately 9.8 cm on average in length and approximately 6.5 cm on average in width.

Leaflets:

*Shape*.—Ovate.

*Margin type*.—Serrate.

*Texture*.—Smooth.

*color*.—Young leaflet: upper surface is commonly near Green Group 137A and under surface is commonly Yellow-Green Group 144A. Mature leaflet: upper surface is commonly near Green Group 139A and under surface is commonly near Yellow-Green Group 147B.

Inflorescence:

*Number of blossoms per cluster*.—Commonly 2-5 on average.

*Typical number of blossoms per plant*.—Commonly more than 15.

*Bloom season*.—Commonly June to October.

*Peduncle*.—Color: commonly near Yellow-Green Group 144A. Size: length is approximately 2.1 cm on average and width is approximately 1.2 mm on average.

*Sepal*.—Size: length is approximately 2.2 cm on average and width at widest point is approximately 5.3 mm on average. Color: upper surface is commonly near Green Group 143C and under surface is commonly near Green Group 138B. Number: commonly 5. Margin type: commonly weak.

*Bud*.—Shape: ovate. Size: length is approximately 1.75 cm on average and diameter is approximately 9.5 mm on average. Color: commonly near Greyed-Orange Group 169A to near Yellow-Orange Group 17C.

*Flower*.—Form: single to semidouble. Petal number: approximately 8 on average. Petal size: approximately 3.3 cm on average in length and approximately 3.1 cm on average in width. Petal shape: generally reniform with an round apex and a round base. Petal margin type: even and smooth. Petal drop: drop clean. Size: approximately 6.5 cm on average in diameter and approximately 2.1 cm on average in depth. Color when opening: outermost petal upper surface is commonly near Orange-Red Group 32C and outermost petal lower surface is commonly near Orange Group 29B. Color when fully open: upper surface is commonly near Orange Group 24D and lower surface is commonly near Orange Group 24D. Fragrance: weak. Stamen number: approximately 80 on average. Anther: approximately 0.92 mm on average in length, approximately 0.37 mm on average in width, sagittate in shape, and color is commonly brown. Filament: approximately 6.7 mm on average in length; approximately 0.48 mm on average in diameter; and commonly light yellow. Pollen: commonly a good amount and color is commonly greyed-yellow. Pistil number: approximately 26 on average. Stigma: approximately 0.26 mm on average in length, approximately 0.34 mm on average in width, shape is irregular round, and color is commonly light brown. Style: length is approximately 1.8 mm on average, diameter is approximately 0.24 mm on average, and color is commonly light yellow.

*Receptacle*.—Shape: pitcher-shape. Size: length is approximately 4.5 mm on average and width is approximately 4.8 mm on average. Color: commonly near Yellow-Green Group 144A with weak anthocyanin.

*Hips/seed*.—Hips are pear-shaped, approximately 0.5 inch in diameter on average, and develop in clusters with approximately 7 seeds per hip.

Development:

*Vegetation*.—Vigorous.

*Blooming*.—Continuous.

*Resistance to diseases*.—Tolerant to black spot *Diplocarpon rosae, Cercosprora rosicola,* downy mildew *Peronospora sparsa*, and rust *Phragmidium* spp.

The new 'VLR001' variety has not been observed under all possible environmental conditions to date. Accordingly, it is possible that the phenotypic expression may vary somewhat with changes in light intensity and duration, cultural practices, and other environmental conditions.

We claim:

1. A new and distinct shrub rose plant characterized by the following combination of characteristics:

(a) abundantly and continuously forms attractive single to semidouble formed orange-red blossoms, (b) exhibits an upright and compact bush growth habit, (c) forms attractive green foliage with a smooth texture, and (d) is well suited for growing as attractive ornamentation in the landscape;

substantially as herein shown and described.

* * * * *